United States Patent
Kristiansen et al.

Patent Number: 4,518,601
Date of Patent: May 21, 1985

[54] 2-(3-PYRIDYL)-1,3,4-OXADIAZOLES AND USE THEREOF IN PEST CONTROL

[75] Inventors: Odd Kristiansen, Möhlin; Jozef Drabek, Oberwil, both of Switzerland

[73] Assignee: Ciba Geigy Corporation, Ardsley, N.Y.

[21] Appl. No.: 502,859

[22] Filed: Jun. 9, 1983

[30] Foreign Application Priority Data

Jun. 16, 1982 [CH] Switzerland ............ 3724/82

[51] Int. Cl.³ .............. A61K 31/42; C07D 413/04
[52] U.S. Cl. ................................ 514/340; 546/277
[58] Field of Search ............... 546/277; 424/263

[56] References Cited

U.S. PATENT DOCUMENTS 2,665,279  1/1954  Aeschlimann et al. ............ 546/277

FOREIGN PATENT DOCUMENTS 1181980  11/1964  Fed. Rep. of Germany .

OTHER PUBLICATIONS

Adv. Het. Chem. 7, § II A-1, 184–193, (pub. date unknown).
Ponticello et al., "Synthesis of 2- and 6-chloro-3-(-5-methyl-1,3,4-oxa . . . ", J. Het. Chem. 17, 425–427 (1980).

Primary Examiner—Jane T. Fan
Attorney, Agent, or Firm—Edward McC. Roberts; Frederick H. Rabin

[57] ABSTRACT

The invention relates to 2-(3-pyridyl)-1,3,4-oxadiazoles of the formula

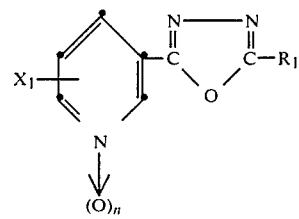

wherein
$R_1$ is hydrogen, $C_1$–$C_6$alkyl, —$COOR_2$ or

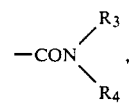

wherein
$R_2$ is $C_1$–$C_6$alkyl
$R_3$ and $R_4$, each independently of the other, are hydrogen or $C_1$–$C_6$alkyl,
$X_1$ is hydrogen, halogen or $C_1$–$C_6$alkyl, and
n is 0 or 1, to the preparation thereof, and to a method of use thereof in pest control.

10 Claims, No Drawings

2-(3-PYRIDYL)-1,3,4-OXADIAZOLES AND USE THEREOF IN PEST CONTROL

The present invention relates to 2-(3-pyridyl)-1,3,4-oxadiazoles, to the preparation thereof, and to a method of use thereof in pest control.

The 2-(3-pyridyl)-1,3,4-oxadiazoles have the formula

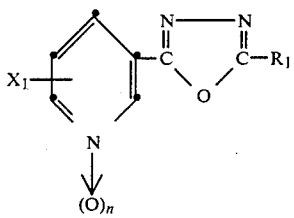

wherein

R is hydrogen, $C_1$–$C_6$alkyl, —$COOR_2$ or

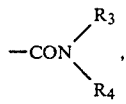

wherein $R_2$ is $C_1$–$C_6$alkyl, $R_3$ and $R_4$, each independently of the other, are hydrogen or $C_1$–$C_6$alkyl, $X_1$ is hydrogen, halogen or $C_1$–$C_6$alkyl, and n is 0 or 1.

Halogen in the above definition is fluorine, chlorine, bromine or iodine.

The alkyl groups $R_1$, $R_2$, $R_3$, $R_4$ and $X_1$ may be straight chain or branched. Examples of such groups comprise: methyl, ethyl, propyl, isopropyl, n-butyl, n-pentyl and n-hexyl, as well as the isomers thereof.

Preferred compounds of formula I are those wherein $R_1$ is hydrogen, $C_1$–$C_3$alkyl, -$COOR_2$ or

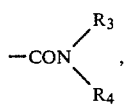

wherein $R_2$ is methyl or ethyl $R_3$ and $R_4$, each independently of the other, are hydrogen, methyl or ethyl, $X_1$ is hydrogen, and n is 0 or 1.

The compounds of formula I can be prepared by methods which are known per se, e.g. in accordance with the following reaction scheme:

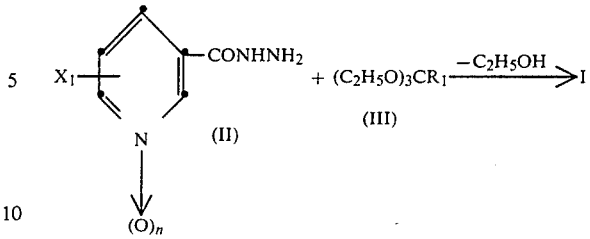

In formulae II and III above, $R_{10}$ $X_1$ and n are as defined for formula I.

The process is carried out in the temperature range from $-50°$ C. to $+180°$ C., preferably from $-10°$ C. to $+160°$ C., under normal or slightly elevated pressure and, if desired, in the presence of a catalytic amount of an acid and of an inert solvent or diluent. Normally, however, the orthoformic acid ester of the formula III suffices as solvent.

Examples of suitable solvents or diluents are: ethers and ethereal compounds such as diethyl ether, diisopropyl ether, dioxan, tetrahydrofuran; aliphatic and aromatic hydrocarbons, preferably benzene, toluene or xylenes; ketones such as acetone, methyl ethyl ketone and cyclohexanone.

The starting materials of the formulae II and III are known or they may be prepared by methods corresponding to known ones.

The compounds of formula I are suitable for controlling pests of animals and plants and soil pests.

In particular, the compounds of the formula I are suitable for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and for controlling phytopathogenic mites and ticks of the order Acarina.

Most particularly, the compounds of the formula I are suitable for controlling plant-destructive insects, especially plant-destructive feeding insects, in ornamentals and crops of useful plants, especially in cotton (e.g. *Spodoptera littoralis* and *Heliothis virescens*) and in crops of vegetables (for example *Leptinotarsa decemlineata* and *Myzus persicae*).

In this connection it is to be emphasised that the above compounds have both a strongly pronounced systemic as well as contact action against sucking insects, and especially against insects of the family Aphididae (e.g. *Aphis fabae, Aphis craccivora* and *Myzus persicae*), which can only be controlled with difficulty using known pesticides.

Compounds of the formula I also have a very advantageous action against flies, e.g. *Musca domestica,* and against mosquito larvae. In addition, the compounds of the formula I have a broad ovicidal and ovilarvicidal action and they have a useful action against ectoparasitic mites and ticks, e.g. of the families Ixodidae, Argasidae and Dermanyssidae.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g., especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radial which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, New Jersey, 1982; and in Dr. Helmut Stache: "Tensid-Taschenbuch, " Carl Hauser Verlag, Munich/Vienna, 1981.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

Formulation Examples

Formulation Examples for liquid active ingredients of the formula I (throughout, percentages are by weight)

| 1 Emulsifiable concentrates | a | b | c |
|---|---|---|---|
| Compound of formula I | 25% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |

-continued

| 1 Emulsifiable concentrates | a | b | c |
|---|---|---|---|
| xylene mixture | 65% | 25% | 20% |

Emulsions of any required concentration can be produced from such concentrates by dilution with water.

| 2 Solutions | a | b | c | d |
|---|---|---|---|---|
| Compound of formula I | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160-190°) | — | — | 94% | — |

These solutions are suitable for application in the form of microdrops.

| 3 Granulates | a | b |
|---|---|---|
| Compound of formula I | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4 Dusts | a | b |
|---|---|---|
| Compound of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| 5 Wettable powders | a | b | c |
|---|---|---|---|
| Compound of formula I | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 6 Emulsifiable concentrate | |
|---|---|
| Compound of formula I | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |

| 6 Emulsifiable concentrate | |
|---|---|
| xylene mixture | 50% |

Emulsions of any required concentration can be obtained from this concentrate by dilution with water.

| 7 Dusts | a | b |
|---|---|---|
| Compound of Formula I | 5% | 8% |
| talcum | 95% | — |
| kaolin | — | 92% |

Dusts which are ready for use are obtained by mixing the active ingredient with the carriers, and grinding the mixture in a suitable mill.

| 8 Extruder granulate | |
|---|---|
| Compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9 Coated granulate | |
|---|---|
| Compound of formula I | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 10 Suspension concentrate | |
|---|---|
| Compound of formula I | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

Preparation of 2-(3-pyridyl)-1,3,4-oxadiazole

A mixture of 15.6 g of nicotinic acid hydrazide, 100 ml of triethyl orthoformate and 0.1 g of potassium hydrogen sulfate is heated in an oil bath to 140° C. and ethyl alcohol is distilled off. After 2 hours, excess triethyl orthoformate is distilled off in a high vacuum. The crude product is purified by chromatography over silica gel with a 1:1 mixture of hexane/toluene as eluant, affording compound 1 of the formula

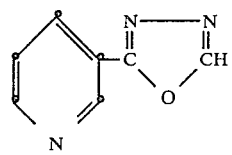

with a melting point of 78°–79° C.

The following compounds are prepared in corresponding manner:

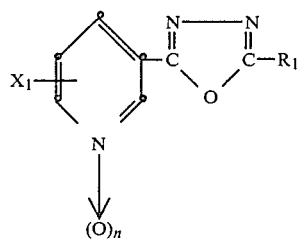

| No. | $R_1$ | $X_1$ | n | Physical data |
|---|---|---|---|---|
| 2 | $CH_3$ | H | 0 | 97–100° C. |
| 3 | $C_2H_5$ | H | 0 | 40–41° C. |
| 4 | $C_3H_{7(n)}$ | H | 0 | 40–41° C. |
| 5 | H | H | 1 | 187–193° C. |
| 6 | $-COOC_2H_5$ | H | 0 | 52–54° C. |
| 7 | $-CON(CH_3)_2$ | H | 0 | $n_D^{20°} = 1.5822$ |

EXAMPLE 2

Systemic isecticidal action against *Aphis craccivora*

Bean plants which have grown roots are transplanted into pots containing 60 ccm of soil and then 50 ml of a solution containing 25 ppm, 5 ppm or 1 ppm of the compound to be tested are poured direct onto the soil.

After 24 hours the parts of the plants above the soil are populated with lice of the species *Aphis craccivora* and a plastic cylinder is then slipped over the plants and tied at the bottom to protect the lice from any possible contact with the test substance either direct or via the gas phase.

A mortality count is made 48 hours after the start of the test. Two plants, each in a separate pot, are used per concentration of test compound. The test is carried out at 25° C. and 70% relative humidity.

The compounds of Example 1 act against insects of the species *Aphis craccivora* as shown in the following table.

Biological test results

The results of the tests carried out in the foregoing Examples are reported in the table, using the following rating to indicate the perentage kill of the pests:

| A: 70–100% kill at a concentration of 1 ppm |
| B: 70–100% kill at a concentration of 5 ppm |
| C: 70–100% kill at a concentration of 25 ppm. |

| Compound No. | *Aphis craccivora* |
|---|---|
| 1 | A |
| 2 | A |
| 3 | A |
| 4 | B |
| 5 | C |
| 6 | B |

-continued

| A: 70–100% kill at a concentration of 1 ppm |
| B: 70–100% kill at a concentration of 5 ppm |
| C: 70–100% kill at a concentration of 25 ppm. |

| Compound No. | *Aphis craccivora* |
|---|---|
| 7 | A |

What is claimed is:

1. A compound of the formula

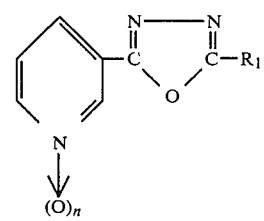

in which:

$R_1$ is hydrogen, $C_1$–$C_3$ alkyl, $-COOR_2$ or

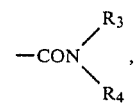

wherein $R_2$ is methyl or ethyl $R_3$ and $R_4$, each independently of the other, are hydrogen, methyl or ethyl, and n is 0 or 1.

2. A compound according to claim 1 of the formula

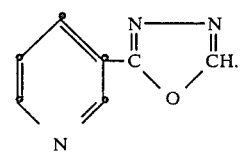

3. A compound according to claim 1 of the formula

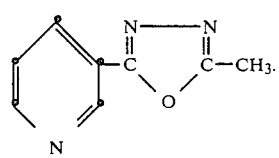

4. A compound according to claim 1 of the formula

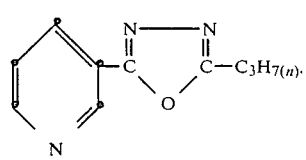

5. A compound according to claim 1 of the formula

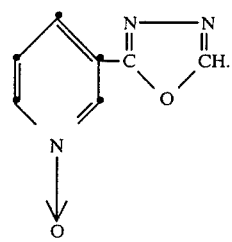

6. A compound according to claim 1 of the formula

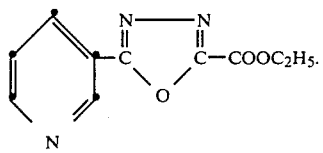

7. A compound according to claim 1 of the formula

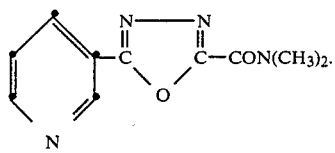

8. An insecticidal and acaricidal composition which comprises (1) a pesticidally effective amount of a compound according to claim 1 as active component, and (2) a carrier.

9. A method for controlling insects and acarids on plants and in the soil which comprises applying to the locus thereof an insecticidally or acaricidally effective amount of a compound of the formula

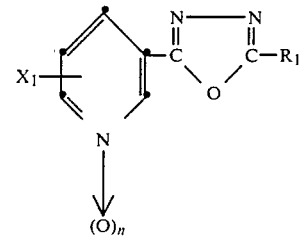

in which $R_1$ is hydrogen, $C_1$–$C_6$ alkyl, —$COOR_2$ or

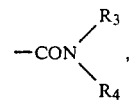

wherein $R_2$ is $C_1$–$C_6$ alkyl, $R_3$ and $R_4$, each independently of the other, are hydrogen or $C_1$–$C_6$ alkyl, $X_1$ is hydrogen, halogen or $C_1$–$C_6$ alkyl, and n is 0 or 1.

10. A method according to claim 9 in which, in the compound, $R_1$ is hydrogen, $C_1$–$C_3$ alkyl, —$COOR_2$ or

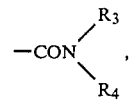

wherein $R_2$ is methyl or ethyl, $R_3$ and $R_4$, each independently of the other, are hydrogen, methyl or ethyl, and $X_1$ is hydrogen.

* * * * *